(12) United States Patent
Moore et al.

(10) Patent No.: US 9,468,417 B1
(45) Date of Patent: Oct. 18, 2016

(54) STENOTIC LESION CHARACTERIZATION

(75) Inventors: Thomas C. Moore, Livermore, CA (US); Kendall R. Waters, Livermore, CA (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 1161 days.

(21) Appl. No.: 13/525,159

(22) Filed: Jun. 15, 2012

Related U.S. Application Data

(60) Provisional application No. 61/497,207, filed on Jun. 15, 2011.

(51) Int. Cl.
```
A61B 8/12       (2006.01)
A61B 5/02       (2006.01)
A61B 8/08       (2006.01)
A61B 5/00       (2006.01)
```

(52) U.S. Cl.
CPC .............. *A61B 8/12* (2013.01); *A61B 5/02007* (2013.01); *A61B 5/0084* (2013.01); *A61B 8/0883* (2013.01); *A61B 8/0891* (2013.01); *A61B 8/5223* (2013.01)

(58) Field of Classification Search
CPC .. A61B 8/12; A61B 5/0066; A61B 5/02007; A61B 8/0891; A61B 2019/5234; A61B 8/06; A61B 8/0883; A61B 8/5223; A61B 8/085; A61B 8/00; A61B 8/08
See application file for complete search history.

(56) References Cited

U.S. PATENT DOCUMENTS

| | | | | |
|---|---|---|---|---|
| 7,165,010 B2 * | 1/2007 | Mancini et al. | ............... | 702/182 |
| 7,753,852 B2 * | 7/2010 | Maschke | ........................ | 600/471 |
| 2009/0204029 A1 * | 8/2009 | Kassab | ......................... | 600/587 |

OTHER PUBLICATIONS

Cox et al., "Atherosclerosis Impairs Flow-Mediated Dilation of Coronary Arteries in Humans", Circulation, vol. 80, No. 3, Sep. 1989, pp. 458-465.*
Corretti et al., "Guidelines for the Ultrasound Assessment of Endothelial-Dependent Flow-Mediated Vasodilation of the Brachial Artery", Journal of the American College of Cardiology, vol. 39, No. 2, 2002, pp. 257-265.*
Tonino et al. "Angiographic versus functional severity of coronary artery stenoses in the FAME study fractional flow reserve versus angiography in multivessel evaluation", J. Am. Coll. Cardiol. 2010;55:2816-2821.
Textbook of Interventional Cardiology by Topol (4th Ed., p. 860).

(Continued)

*Primary Examiner* — Katherine Fernandez
(74) *Attorney, Agent, or Firm* — Fredrikson & Byron, P.A.

(57) ABSTRACT

An intravascular measurement device can be used to characterize a stenotic lesion in the body of a patient. In some examples, the intravascular measurement device is inserted into the patient and used to measure a physical dimension (e.g., diameter, cross-sectional area) of a blood vessel having the stenotic lesion during non-hyperemic blood flow. Thereafter, a pharmacologic vasodilator drug is introduced into the body of the patient so as to cause the patient to exhibit hyperemic blood flow rates. The intravascular measurement device may then be used to again measure the physical dimension of the blood vessel having the stenotic lesion, this time during hyperemic blood flow. A comparison between the physical dimension of the blood vessel during non-hyperemic and hyperemic blood flow can be used to characterize the stenotic lesion.

23 Claims, 3 Drawing Sheets

(56) References Cited

OTHER PUBLICATIONS

Kiviniemi et al. "Vasodilation of epicardial coronary artery can be measured with transthoracic echocardiography", Ultrasound in Med. & Biol. 2007;33:362-370.

Jasti et al. "Correlations Between Fractional Flow Reserve and Intravascular Ultrasound in Patients With an Ambiguous Left Main Coronary Artery Stenosis", Circulation. 2004;110:2831-2836.

* cited by examiner

STENOTIC LESION CHARACTERIZATION

This application claims the benefit of U.S. Provisional Patent Application No. 61/497,207, filed Jun. 15, 2011, the entire content of which is incorporated herein by reference.

TECHNICAL FIELD

This disclosure relates to stenotic lesions and, more particularly, to intravascular measurement devices and techniques for characterizing stenotic lesions.

BACKGROUND

Assessing the severity of a stenotic lesion is an important part of recommending a treatment option. In some instances, if the stenotic lesion is permitted to grow unchecked, it can lead to a blockage of blood flow which can cause a variety of very significant problems. Common treatment options, such as a stent, angioplasty, etc. are often recommended to inhibit or roll back growth of a stenotic lesion. That said, treatment options can result in their own negative consequences. Thus, if the characteristics of the stenotic lesion are such that they have a minimal impact on the flow of blood through the vessel, it may be recommended to monitor the stenotic lesion over time but take no intervening action other than to administer drug therapy. Angiograms are common methods of assessing the severity of a stenotic lesion, but, in many cases, there is a desire for additional means of gathering information to more fully characterize the stenotic lesion.

SUMMARY

In general, this disclosure is directed to techniques for evaluating and/or characterizing a stenotic lesion to determine whether or not the lesion is inducing ischemia. If a lesion is determined to be inducing ischemia, a healthcare provider may take a comparatively aggressive treatment approach, such as performing angioplasty or inserting a stent to treat the lesion. On the other hand, if the lesion is not determined to be inducing ischemia, the healthcare provider may adopt a more passive treatment approach, such as drug therapy and future monitoring of the lesion.

In some examples in which a stenotic lesion is characterized according to the present disclosure, an intravascular measurement device is inserted into a region of a blood vessel that has the lesion. The intravascular measurement device may be used to measure a physical dimension of the blood vessel at one or more locations in the blood vessel. For example, the intravascular measurement device may be used to measure a physical dimension of the blood vessel at a location distal to the stenotic lesion, a location proximal to the stenotic lesion, and/or a location in the region of the stenotic lesion where the blood vessel defines a minimal lumen diameter (e.g., a location where the lesion causes the maximum narrowing of the blood vessel lumen). The intravascular measurement device may measure the physical dimension of the blood vessel at a first condition, such as when a first blood flow rate is passing through the blood vessel, and again at a second condition, such as when a second blood flow rate greater than the first blood flow rate is passing through the blood vessel. The first blood flow rate may be a natural blood flow rate through the patient (e.g., without the influence of external agents that may influence the blood flow rate) whereas the second blood flow rate may be an artificially increased blood flow rate (e.g., a maximal hyperemic blood flow rate). A stenotic lesion that is not ischemia inducing may exhibit a change in physical dimension between the first condition (e.g., blood flow rate) and the second condition that is different than a change in physical dimension exhibited by an ischemia-inducing lesion. In this way, the intravascular measurement device may be used to determine whether or not a stenotic lesion is ischemia inducing.

In one example, a method is described that includes receiving a first measurement signal from an intravascular measurement device, the first measurement signal being indicative of a physical dimension of a blood vessel having a stenotic lesion during a first blood flow rate. The method includes receiving a second measurement signal from the intravascular measurement device, the second measurement signal being indicative of the physical dimension of the blood vessel having the stenotic lesion during a second blood flow that is greater than the first blood flow rate. According to the example, the method further includes determining, with a processor, a value representative of a change in the physical dimension of the blood vessel between the first blood flow rate and the second blood flow rate based on the first measurement signal and the second measurement signal.

In another example, a system is described that includes an intravascular measurement device, a catheter configured to deliver the intravascular measurement device to a desired location in a body of a patient, and a processor. According to the example, the processor is configured to receive a first measurement signal from the intravascular measurement device, the first measurement signal being indicative of a physical dimension of a blood vessel having a stenotic lesion during a first blood flow rate, receive a second measurement signal from the intravascular measurement device, the second measurement signal being indicative of the physical dimension of the blood vessel having the stenotic lesion during a second blood flow rate that is greater than the first blood flow rate, and determine a value representative of a change in the physical dimension of the blood vessel between the first blood flow rate and the second blood flow rate based on the first measurement signal and the second measurement signal.

In another example, a non-transitory computer-readable medium is described that includes instructions for causing a programmable processor to receive a first measurement signal from an intravascular measurement device and receive a second measurement signal from the intravascular measurement device. The first measurement signal is indicative of a physical dimension of a blood vessel having a stenotic lesion during a first blood flow rate, and the second measurement signal is indicative of the physical dimension of the blood vessel having the stenotic lesion during a second blood flow that is greater than the first blood flow rate. According to the example, the computer-readable medium also includes instructions for causing a programmable processor to determine a value representative of a change in the physical dimension of the blood vessel between the first blood flow rate and the second blood flow rate based on the first measurement signal and the second measurement signal.

In another example, a method is described that includes inserting an intravascular measurement device into a body of a patient and measuring via the intravascular measurement device a physical dimension of a blood vessel having a stenotic lesion during a non-hyperemic blood flow rate. The method further includes introducing a pharmacologic vasodilator drug into the body of the patient so as to cause the patient to exhibit hyperemic blood flow rates and measuring via the intravascular measurement device the physical dimension of a blood vessel having the stenotic lesion during a hyperemic blood flow rate.

The details of one or more examples are set forth in the accompanying drawings and the description below. Other features, objects, and advantages will be apparent from the description and drawings, and from the claims.

DETAILED DESCRIPTION

Figure 1:
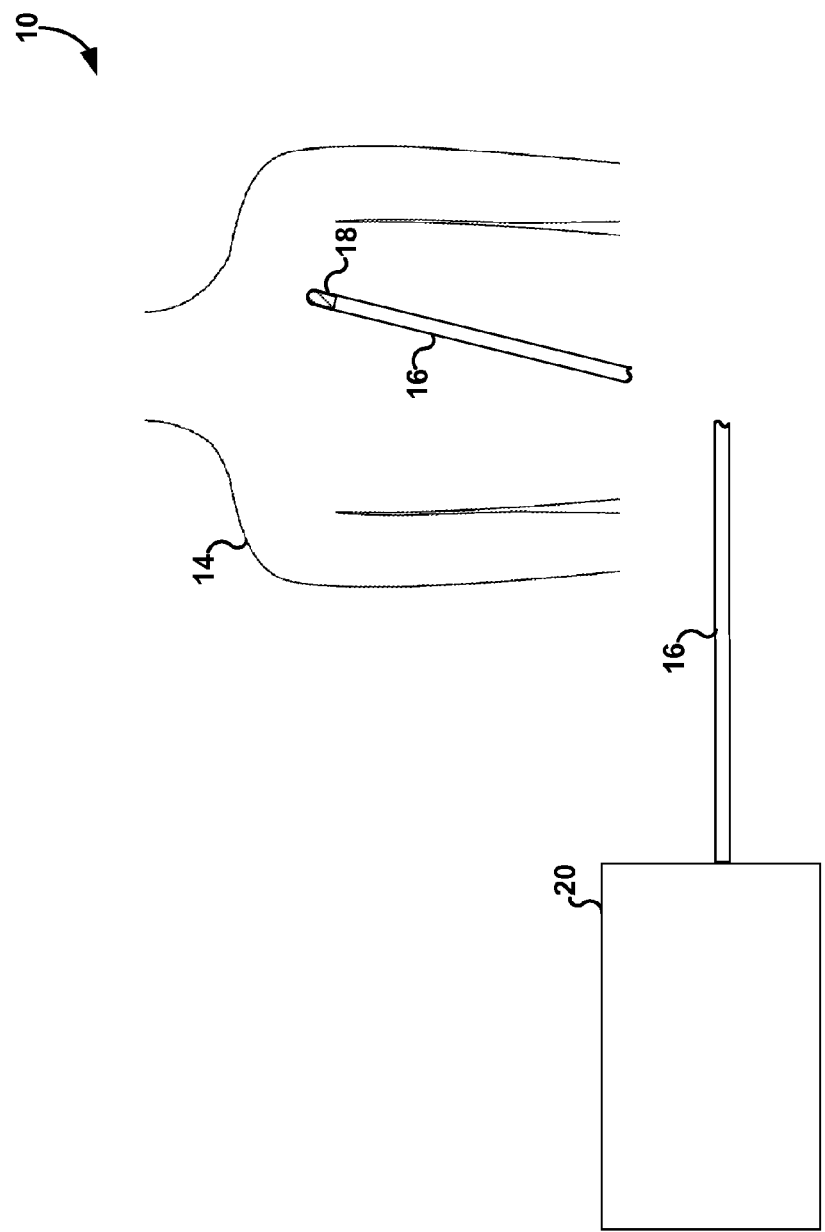
FIG. 1 is a conceptual diagram illustrating an example system comprising an intravascular measurement device that may be used to evaluate a stenotic lesion in a patient.

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes may be provided for selected elements, and all other elements employ that which is known to those of skill in the field. Those skilled in the art will recognize that many of the examples provided have suitable alternatives that can be utilized.

Ischemic heart disease, which may also be referred to as myocardial ischemia, is a disease characterized by reduced blood supply to the heart muscle. Ischemic heart disease can occur due when a wall of a coronary artery thickens, e.g., due to the accumulation of fatty materials such as cholesterol. Regions of an artery or other blood vessel that are abnormally narrowed, for example due to accumulated fatty deposits, are typically referred to as stenotic lesions. Although stenotic lesions narrow the flow path through a blood vessel, thereby restricting fluid movement through the blood vessel, some stenotic lesions have minimal impact on the flow of blood through the vessel. These types of lesions are typically monitored without taking further invasive action because risk that the lesions will grow to the point of causing ischemia, or a restriction in blood supply to tissue, is relatively low. By contrast, other types of lesions have characteristics that either cause ischemia, for example by restricting blood flow to a heart organ or other tissue, or are likely to cause ischemia. These types of lesions, which may be referred to as ischemia-inducing lesions, are typically treated through more aggressive interventional procedures, such as angioplasty or stent placement, to help remove the blockage and restore blood supply to the tissue. Being able to accurately evaluate and characterize a lesion in a patient may be useful to ensure that the patient receives the appropriate treatment corresponding to the severity of the lesion.

This disclosure describes devices, systems, and techniques for evaluating and/or characterizing a lesion in a patient. In some examples as described herein, a lesion characterization system includes an intravascular measurement device that can be inserted through the vascular structure of a patient to a location where there is a stenotic lesion. In different examples, the intravascular measurement device may be an intravascular ultrasound device (IVUS), an intravascular optical device such an intracoronary optical coherence tomography device, or yet a different type of intravascular measurement device. Regardless, once positioned at a desired anatomical location relative to the stenotic lesion, the intravascular measurement device can be used to measure a physical dimension of the blood vessel within the stenotic lesion. For example, the intravascular measurement device may be used to measure a diameter, a cross-sectional area, and/or a volume of either the stenotic lesion itself or a region proximate the stenotic lesion. In some applications, the intravascular measurement device is used to measure physical dimensions of the blood vessel at multiple different locations relative to the stenotic lesion, such as a physical dimension of the blood vessel at a location distal to the stenotic lesion and a physical dimension of the blood vessel at a location proximal to the stenotic lesion.

Independent of the specific physical dimension measured or the specific anatomical location being measured, at least two physical measurements at a specific anatomical location may be taken under different physiological conditions. For example, the intravascular measurement device may measure a blood vessel within a stenotic lesion at a specific location or locations of under a first set of physiological conditions and then re-measure the blood vessel at the same location or locations under a second set of physiological conditions that are different than the first set of physiological conditions. The change in physical dimensions of the blood vessel caused by the changing physiological conditions may indicate whether or not the stenotic lesion being evaluated is likely to induce ischemia. That is, the physical dimensions of the blood vessel being measured may change a certain amount if the stenotic lesion is an ischemia-inducing lesion while the physical dimensions of the blood vessel may change a different amount if the stenotic lesion is nonischemic. In turn, the determination of whether the stenotic lesion is ischemic or nonischemic may dictate how the stenotic lesion is subsequently treated.

FIG. 1 is a conceptual diagram illustrating an example system 10 that may be used to evaluate and/or characterize a stenotic lesion in the body of patient 14. System 10 includes a catheter 16, an intravascular measurement device 18, and a console 20. Intravascular measurement device 18 can be inserted into the body of patient 14 and used to measure various anatomical characteristics within patient 14. For example, intravascular measurement device 18 can be used to measure a physical dimension of a blood vessel of patient 14. In the example of FIG. 1, intravascular measurement device 18 is shown positioned within a coronary artery of patient 14 and connected via catheter 16 to console 20, which is positioned outside of the body of patient 14. In other examples, intravascular measurement device 18 can be positioned in other arteries, blood vessels, or body lumens that contain a lesion. Console 20 may house various operating components of system 10 that control the operation of intravascular measurement device 18, send signals to or receive signals from the intravascular measurement device, store data generated by or used with the intravascular measurement device, or the like. In some examples, console 20 also includes a user interface that allows a clinician to interact with intravascular measurement device 18 and/or display information generated by the intravascular measurement device.

As described in greater detail below, a clinician may insert intravascular measurement device 18 into a blood vessel of patient 14 that has a stenotic lesion. Once intravascular measurement device 18 is positioned at a desired location in the blood vessel relative to a stenotic lesion, the clinician may use the intravascular measurement device to make at least two measurements of the blood vessel under at least two different conditions. For example, the clinician may use intravascular measurement device 18 to make a first measurement at a specific location in the blood vessel under a first set of conditions and then use the intravascular measurement device to make a second measurement at the same specific location in the blood vessel under a second set of conditions. In some examples, the first set of conditions is a first blood flow rate passing through the blood vessel and the second set of conditions is a second blood flow rate passing through the blood vessel that is higher than the first blood flow rate. For example, the first blood flow rate may be a normal (e.g., non-hyperemic) blood flow rate and the second blood flow rate may be a hyperemic blood flow rate. Among other techniques, a clinician may induce hyperemia in patient 14, e.g., by administering a vasodilation agent, to cause the change in blood flow rate. System 10 may compare a blood vessel measurement determined by intravascular measurement device 18 under the first set of conditions to a blood vessel measurement determined by the intravascular measurement device under the second set of conditions. System 10 may determine whether the stenotic lesion within the blood vessel is ischemic or nonischemic based on the comparison.

During use, intravascular measurement device 18 of system 10 may be positioned within a lumen of the body of patient 14 and used to measure the lumen into which the device is positioned. For example, intravascular measurement device 18 may measure a physical dimension of the lumen into which the device is positioned. As described in greater detail below, intravascular measurement device 18 may emit energy into the body lumen into which the device is positioned. Different objects within the body (e.g., different tissues) may absorb, transmit, and reflect different amounts of the emitted energy. Accordingly, intravascular measurement device 18 may receive emitted energy that is reflected back from the different bodily objects and determine based on the received energy (e.g., the magnitude and/or timing of the received energy) a physical dimension of the bodily lumen into which the device is inserted.

In some examples, intravascular measurement device 18 emits energy radially 360 degrees around the device and receives reflected energy from bodily structure positioned around the circumference of the device. For example, intravascular measurement device 18 may emit energy radially in one direction while being rotated at least one revolution so as to emit the energy 360 degrees around the device. In another example, intravascular measurement device 18 may include multiple energy emitters positioned so as to direct energy in a plurality of radial directions around the device. The multiple energy emitters may emit energy simultaneously or the multiple energy emitters may emit energy at different times. In some examples, each of the multiple energy emitters emits energy at a different time, effectively providing a rotating energy beam around the perimeter of the device that is created by controlling the electrical activation and deactivation of different energy emitters. By emitting energy around an entire perimeter of intravascular measurement device 18, the device may determine physical dimensions of the lumen into which the device is inserted in different directions rather than only a single direction. This information can be used to determine a diameter of the lumen into which intravascular measurement device 18 is positioned, a cross-sectional area of the lumen, or other physical dimensions. For instance, when intravascular measurement device 18 is translated axially along a length of the lumen while emitting energy and receiving reflected energy, the device may determine a volume of the lumen (or a portion of the lumen) based on the length of axial translation and determined cross-sectional area of the lumen.

Intravascular measurement device 18 can be implemented using any suitable device. In one example, intravascular measurement device 18 is an intravascular ultrasound device (IVUS). An intravascular ultrasound device can emit acoustical energy at an ultrasonic frequency or frequencies and receive back a reflected portion of the emitted ultrasonic pressure wave. In another example, intravascular measurement device 18 is an intravascular optical measurement device. An intravascular optical measurement device can emit optical energy (e.g., light) and receive back a reflected portion of the optical energy. An optical coherence tomography device is an example of an intravascular optical measurement device. In different examples, intravascular measurement device 18 may or may not be configured to image the blood vessel of patient 14 into which the device is inserted.

Catheter 16 connects intravascular measurement device 18 to console 20. Catheter 16 may define a lumen that allows signals to communicate from console 20 to intravascular measurement device 18 and also allows signals to communicate from intravascular measurement device 18 to console 20, e.g., via one or more communication lines (e.g., electrical, optical, and/or fluid communication lines) extending along the length of the catheter. Catheter 16 can comprise a unitary catheter or a plurality of catheter segments connected together to form an overall catheter length. In the example of FIG. 1, catheter 16 traverses from console 20 to a target measurement site within patient 14.

The specific configuration of catheter 16 may vary depending, e.g., on the type of intravascular measurement device 18 used in system 10. In instances in which intravascular measurement device 18 is an intravascular ultrasonic measurement device, catheter 16 may be a mechanical rotating catheter or an array catheter. With a mechanically rotating catheter, the catheter can mechanically rotate an ultrasonic emitter and/or receiver of intravascular measurement device 18 within a catheter sheath that is transparent to the frequency of ultrasonic energy being emitted and/or received. As the catheter rotates the ultrasonic emitter and/or receiver, an ultrasonic beam sweeps across a region of interest generating data representative of the physical dimensions of the lumen into which the catheter is inserted. With an array catheter, a plurality of ultrasonic emitters and/or receivers can be positioned (e.g., ringed) about the perimeter of the catheter so as to generate data representative of the physical dimensions of the lumen into which the catheter is inserted without physically rotating an ultrasonic emitter and/or receiver.

During evaluation of a stenotic lesion in patient 14 using system 10, a clinician may catheterize the patient and deliver intravascular measurement device 18 via catheter 16 to a target measurement location. Depending on the application, the clinician may first deliver a guidewire to an area of interest in patient 14 (e.g., an area that includes the stenotic lesion) and then deliver catheter 16 over the guidewire. Regardless, once suitably positioned within patient 14, the clinician may use system 10 (e.g., intravascular measurement device 18 of system 10) to measure various physical dimensions within the region of the patient that includes the stenotic lesion.

Figure 2:
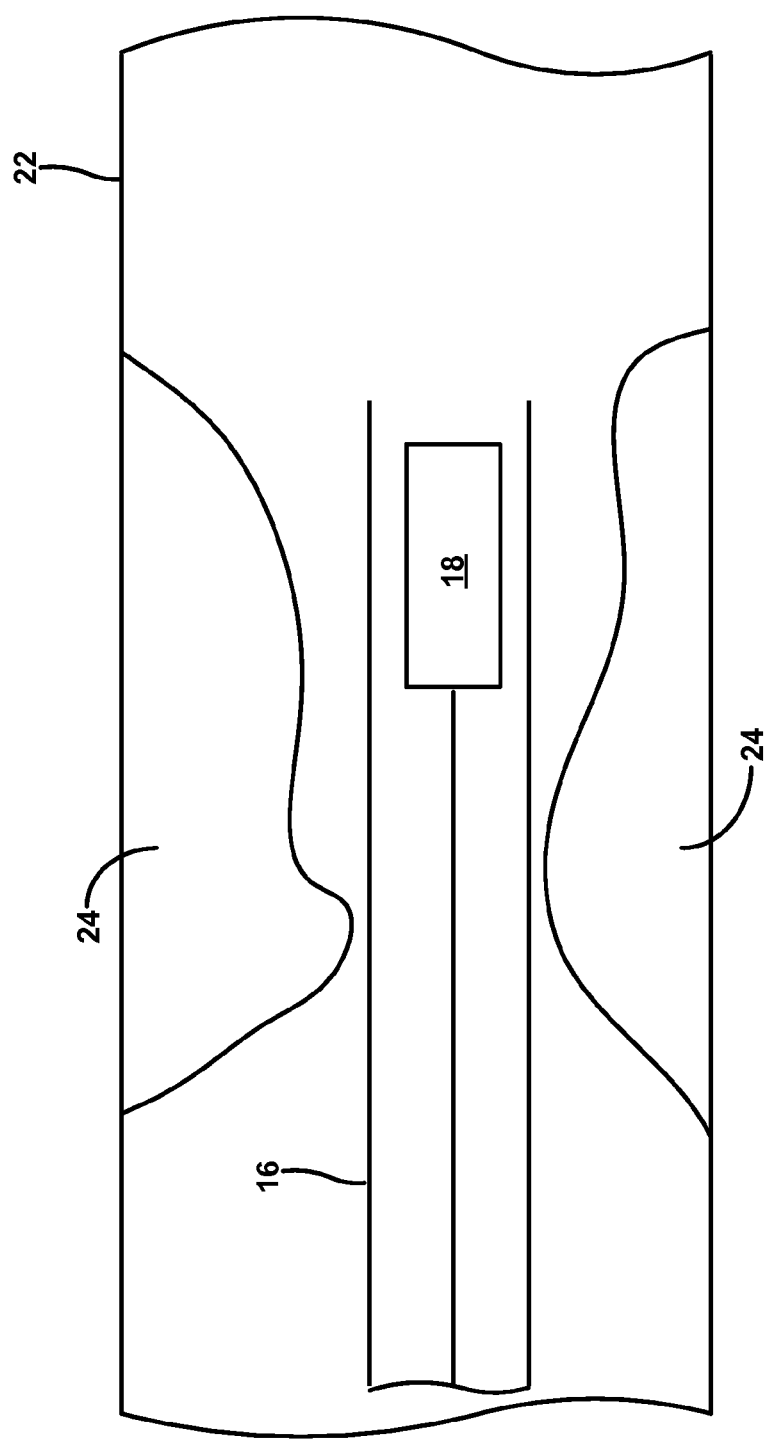
FIG. 2 is cross-sectional conceptual diagram illustrating the intravascular measurement device of FIG. 1 positioned in an example blood vessel.

FIG. 2 is a cross-sectional schematic showing an example portion of a blood vessel 22 having a stenotic lesion 24. Intravascular measurement device 18 is inserted into blood vessel 22 to measure a physical dimension of the blood vessel in a region proximate stenotic lesion 24. In particular, in the example of FIG. 2, intravascular measurement device 18 is inserted into blood vessel 22 so as to measure a physical dimension of the blood vessel a location distal to stenotic lesion 24. A location may be distal to stenotic lesion 24 in that intravascular measurement device 18 may need to traverse past the stenotic lesion in order to measure a physical dimension of the location. In other examples, intravascular measurement device 18 is inserted into blood vessel 22 so as to measure a physical dimension of the blood vessel a location proximal to stenotic lesion 24. A location may be proximal to stenotic lesion 24 in that intravascular measurement device 18 may measure a physical dimension of the location without traversing past the stenotic lesion. That is, as intravascular measurement device 18 is advanced into the body of patient 14 (FIG. 1), the intravascular measurement device may encounter the region proximal to stenotic lesion 24 prior to encountering the stenotic lesion itself as the device is advanced axially forward in the body.

In general, measuring a physical dimension of blood vessel 22 in the region proximate stenotic lesion 24 may be useful for characterizing the lesion and, in some examples, determining whether or not the lesion is ischemic. A physical dimension of blood vessel 22 may indicate to a clinician the amount of constriction (e.g., narrowing) of the blood vessel caused by stenotic lesion 24. Accordingly, with knowledge of the physical dimension of blood vessel 22, a clinician can assess how much impact stenotic lesion has on the physiology of patient 14 (FIG. 1) and determine an appropriate treatment regime.

In some examples as described in the present disclosure, intravascular measurement device 18 may be used to make multiple (e.g., at least two) measurements of a physical dimension of blood vessel 22 in a region proximate stenotic lesion 24, where each measurement is made at the same (or substantially the same) location within patient 14 and each measurement is made under different conditions (e.g. physiological conditions). For example, intravascular measurement device 18 may be used to make multiple measurements of a physical dimension of blood vessel 22 in a region proximate stenotic lesion 24, where each measurement is made at the same (or substantially the same) location within patient 14 and each measurement is made with different blood flow rates passing through the blood vessel being measured. In such an example, intravascular measurement device 18 may measure blood vessel 22 at a specific location in the blood vessel when a first rate of blood is flowing through the vessel and intravascular measurement device 18 may re-measure blood vessel 22 at the same (or substantially the same) specific location in the blood vessel when a second rate of blood is flowing through the vessel. The second rate of blood flow may be higher or lower than the first rate of blood flow, depending on the specific application.

Without being bound by any particular theory, it is believed that a change in physical dimensions of a blood vessel and/or lesion in response to changing physiological conditions within a patient (e.g., changing blood flow rates), may be different for an ischemia-inducing lesion than for a lesion that does not induce ischemia. For example, when blood vessel 22 is measured in a region proximate stenotic lesion 24 at a first blood flow rate, the blood vessel may be expected to have a certain physical dimension. Increasing the blood flow rate through blood vessel 22 may be expected to increase the physical dimension of the blood vessel because pressure within the blood vessel caused by the increased flow rate may expand the blood vessel outward. The amount blood vessel 22 expands in response to increasing blood flow rates may vary depending on how much the walls of the blood vessel have hardened, e.g., due to calcification. For example, in instances in which blood vessel 22 has a lesion that is characterized as ischemia-inducing, the wall of the blood vessel may expand less than instances in which the lesion is characterized as not being ischemia-inducing. In this manner, making multiple measurements of a physical dimension of blood vessel 22 in a region proximate stenotic lesion 24, where each measurement is made under different conditions (e.g. physiological conditions) may be useful to determine whether or not a lesion is ischemic-inducing.

In other examples, intravascular measurement device 18 may be used to make multiple (e.g., at least two) measurements of a physical dimension of blood vessel 22 in at least two different locations within the region proximate stenotic lesion 24, where each measurement is made under the same (or substantially the same) conditions (e.g. physiological conditions). For example, intravascular measurement device 18 may be used to make a measurement of blood vessel 22 at a location distal to stenotic lesion 24 and also at a location proximal to the lesion. Both measurements may be made under the same conditions (e.g., same blood flow rates). Comparison of measurements made under the same conditions at different locations within blood vessel 22 may also be useful for determining whether or not a lesion is ischemic-inducing.

In examples in which measurements are made under different conditions, a variety of different techniques can be used to establish different conditions under which to measure a physical dimension of blood vessel 22. In one example, intravascular measurement device 18 measures blood vessel 22 at one or more locations at a first blood flow rate and then again measured the blood vessel at the same one or more locations at a second blood flow rate that is different (e.g., greater) than the first blood flow rate. The first blood flow rate may be a normal (e.g., non-hyperemic) blood flow rate and the second blood flow rate may be a hyperemic blood flow rate. For example, the first blood flow rate may be a natural blood flow rate through the patient (e.g., without the influence of external agents that may influence the blood flow rate) and the second blood flow rate may be an artificially increased blood flow rate (e.g., a maximal hyperemic blood flow rate).

In some examples, a clinician may vary the blood flow rate of patient 14 by administering a pharmacologic vasodilator drug such as adenosine to the patient. As the vasodilatory drug enters the patient's blood stream, the drug may cause vasodilation, or an opening of the patient's blood vessels. In turn, this may reduce resistance to blood flow through the patient's blood vessel, resulting in an increase in blood flow through the blood vessel. In accordance with this example, a clinician may use intravascular measurement device 18 to determine physical dimensions of blood vessel 22 at one or more locations in a region proximate stenotic lesion 24 prior to administration of a vasodilator drug. The clinician may then introduce the vasodilator drug into the patient (e.g., by administering an oral agent or injecting a drug) and wait until the patient exhibits hyperemic blood flow conditions (e.g., maximal hyperemia when blood flow is the greatest). When suitable hyperemic blood flow conditions are achieved, the clinician may use intravascular measurement device 18 to determine the physical dimensions of blood vessel 22 at the one or more locations measured prior to administration of the vasodilator drug.

Although a clinician can administer a vasodilatory drug like adenosine to increase blood flow rates in a patient, the process of administering the drug and waiting for the drug to take effect can add substantial amounts of time to the characterization procedure. Further, some patients report discomfort when receiving vasodilatory drugs. For these and other reasons, some care providers may prefer to avoid administering a vasodilatory drug to patients when assessing the severity of a stenotic lesion.

Accordingly, in some examples, a clinician may use intravascular measurement device 18 to measure blood vessel 22 at one or more locations without administering a vasodilatory drug. Instead, the clinician (or a device in system 10 in FIG. 1) may monitor a parameter indicative of nature blood conduction through patient 14 (FIG. 1) and use intravascular measurement device 18 to measure blood vessel 22 during transient periods when blood flow rates are comparatively low and comparatively high. Blood flow rate variations may occur in the body due to the discontinuous mechanical pumping action of the heart. For example, a blood flow rate through blood vessel 22 during a period corresponding to diastole, when the heart is refilling with blood, may be lower than a blood flow rate through blood vessel 22 during a period corresponding to systole, when the heart is contracting.

Because a patient's cardiac cycle is indicative of changes in blood flow rate or blood pressure that occurs from the beginning of one heartbeat to the next heartbeat, in some examples, a physical dimension of blood vessel 22 is measured via intravascular measurement device 18 during a first part of a patient's cardiac cycle (e.g., when blood flow rate is comparatively low) and again during a second part of the cardiac cycle (e.g., when blood flow rate is higher as compared to the first part of the cardiac cycle). In some examples, the second part of the cardiac cycle is a portion of the cardiac cycle in which resistance to fluid flow in the vascular system of patient 14 is minimal.

Measuring a physical dimension of blood vessel 22 during a specific portion of a cardiac cycle may be a variation of a technique known to those skilled in the art that measures pressure drop across a stenotic lesion without using vasodilatory drugs. This method, called the instant wave-Free Ratio (iFR), relies on a short segment of the coronary waveform in which the downstream resistance to blood flow is relatively stable. When applied in some examples of the present disclosure, intravascular measurement device 18 may measure a physical dimension of blood vessel 22 at one or more locations during a portion of the cardiac cycle where there are no proximally-originating (e.g., from the ventricle and aorta of the heart) or distally-originating (e.g., from the microvascular) pressure waves propagating through blood vessel 22. This measurement may be indicative of a physical dimension of blood vessel 22 at a comparative high blood flow rate. Intravascular measurement device 18 may measure a physical dimension of blood vessel 22 at the one or more locations during a different portion of the cardiac cycle to generate a measurement indicative of the physical dimension of blood vessel 22 at a comparative low blood flow rate.

As briefly discussed above, intravascular measurement device 18 can be used to measure a physical dimension of blood vessel 22 at a variety of different locations within the region of stenotic lesion 24. In some examples, intravascular measurement device 18 may be used to measure a physical dimension of blood vessel 22 at multiple (e.g., two, three, four, or more) locations within the region of stenotic lesion 24. In general, the specific location within blood vessel 22 that a clinician will use intravascular measurement device 18 to measure may vary, e.g., depending on the characteristics of the lesion being examined, the location of the lesion, and other clinically relevant factors.

In one example, intravascular measurement device 18 is inserted into blood vessel 22 to measure a physical dimension of the blood vessel at a location distal to stenotic lesion 24. If stenotic lesion 24 is well defined with a non-diseased section of blood vessel 22 located distally from the lesion, intravascular measurement device 18 may measure a physical dimension of distally located non-diseased section of blood vessel (e.g., a section of the non-diseased blood vessel closest to the stenotic lesion in the distal direction). By contrast, if stenotic lesion 24 is not well defined such that it is difficult to identify a distally located section of non-diseased blood vessel, the clinician may measure blood vessel 22 at a defined location that is distal from where stenotic lesion 24 causes a maximum narrowing of the blood vessel lumen. For example, clinician may measure blood vessel 22 at a distal location that ranges from approximately 5 millimeters (mm) to approximately 50 mm (e.g., from approximately 10 mm to approximately 20 mm) from a location where stenotic lesion 24 causes a maximum narrowing of the blood vessel lumen. This measurement may be considered a measurement of blood vessel 22 at a location distal to stenotic lesion 24.

In another example, intravascular measurement device 18 is inserted into blood vessel 22 to measure a physical dimension of the blood vessel at a location proximal to stenotic lesion 24. If stenotic lesion 24 is well defined with a non-diseased section of blood vessel 22 located proximally from the lesion, intravascular measurement device 18 may measure a physical dimension of proximally located non-diseased section of blood vessel (e.g., a section of the non-diseased blood vessel closest to the stenotic lesion in the proximal direction). By contrast, if stenotic lesion 24 is not well defined such that it is difficult to identify a proximally located section of non-diseased blood vessel, the clinician may measure blood vessel 22 at a defined location that is proximal from where stenotic lesion 24 causes a maximum narrowing of the blood vessel lumen. For example, clinician may measure blood vessel 22 at a proximal location that ranges from approximately 5 millimeters (mm) to approximately 50 mm (e.g., from approximately 10 mm to approximately 20 mm) from a location where stenotic lesion 24 causes a maximum narrowing of the blood vessel lumen. This measurement may be considered a measurement of blood vessel 22 at a location proximal to stenotic lesion 24.

In yet another example, intravascular measurement device 18 is inserted into blood vessel 22 to measure a physical dimension of the blood vessel at a location where stenotic lesion 24 is present. Although a variety of locations of blood vessel 22 can be measured where stenotic lesion 24 is present, in some examples, the blood vessel is measured where stenotic lesion 24 causes a maximum narrowing of the blood vessel lumen. This position may be representative of the narrowest flow pathway through which blood can pass through blood vessel 22. It should be appreciated that a clinician may not know where in blood vessel 22 stenotic lesion 24 causes maximum narrowing until the clinician determines physical dimensions of the entire region of the blood vessel proximate the stenotic lesion. Therefore, although intravascular measurement device 18 is described as being used to measure blood vessel 22 at discrete locations within the blood vessel, in some examples, intravascular measurement device 18 may measure multiple dimensions along the length of the blood vessel. For example, during use, intravascular measurement device 18 may traverse along an axial length of blood vessel 22 from a region distal to stenotic lesion 24, through the region of the blood vessel in which the stenotic lesion is present, and to a region proximal to the stenotic lesion. Intravascular measurement device 18 may image the entire length of blood vessel 22 as the device is traversed, thereby providing different physical dimension measurements along the length of the blood vessel. Specific measurements can then be selected from the different physical dimension measurements (e.g., specific measurements corresponding to specific locations within blood vessel 22) for use in subsequent calculations to characterize stenotic lesion 24.

Depending on the application, intravascular measurement device 18 may be inserted into blood vessel 22 to measure physical dimension of the blood vessel at multiple locations along the length of the blood vessel. Measuring physical dimensions of blood vessel 22 at multiple locations may be useful in that a change in dimension at one location relative to a change in dimension at another location in response to changing conditions (e.g., different blood flow rates) may vary depending on whether or not stenotic lesion 24 is ischemia inducing. In one example, intravascular measurement device 18 is used to measure a physical dimension of blood vessel 22 at both a location distal to stenotic lesion 24 and a location proximal to the stenotic lesion. Without being bound by theory, it is believed that for a normal vessel that does not cause ischemia, a relative change (e.g., caused by a change in blood flow rate) in physical dimension of blood vessel 22 at a location distal to stenotic lesion 24 may be approximately the same as compared to a relative change in physical dimension of the blood vessel at a location proximal to stenotic lesion 24. For an ischemia-inducing lesion, however, a relative change (e.g., caused by a change in blood flow rate) in physical dimension of blood vessel 22 at the location distal to stenotic lesion 24 may be smaller than the relative change in physical dimension of the blood vessel at the location proximal to stenotic lesion 24. For example, increasing blood flow rate through blood vessel 22 will cause the blood vessel to dilate more in a region proximal to stenotic lesion 24 than in a region distal to the lesion for an ischemia-inducing lesion as compared to a lesion that does not induce ischemia.

In response to data generated by intravascular measurement device 18, system 10 can determine a physical dimension of blood vessel 22 into which the device is inserted. Example physical dimensions that may be determined by system 10 include a diameter of blood vessel 22 (e.g., internal diameter) at a specific location of measurement and/or a cross-sectional area (e.g., an internal cross-sectional area) at the specific of the measurement. In instances in which physical dimensions of blood vessel 22 are measured along an axial length of the blood vessel, system 10 may determine a volume of a portion of the blood vessel (e.g., a proximal portion, a distal portion, a portion where stenotic lesion 24 causes a maximum narrowing of the blood vessel lumen) by multiplying a length of the blood vessel by a determined cross-sectional area over that length.

With further reference to FIG. 1, data generated by intravascular measurement device 18 may be transmitted through catheter 16 to console 20. Console 20 may house various processing hardware and/or software and operating components of system 10. For example, console 20 may house hardware and/or software that control the operation of intravascular measurement device 18 via control signals that are transmitted through catheter 16. Intravascular measurement device 18 may make measurements in response to instructions received from console 20 and transmit data indicative of a physical dimension of a lumen of patient 14 back to the console. For example, a clinician may provide user input to console 20 (e.g., pressing a button or activating a switch) that causes intravascular measurement device 18 to make measurements in response to instructions received from console 20 and transmit data indicative of a physical dimension of a lumen of patient 14 back to the console.

Figure 3:
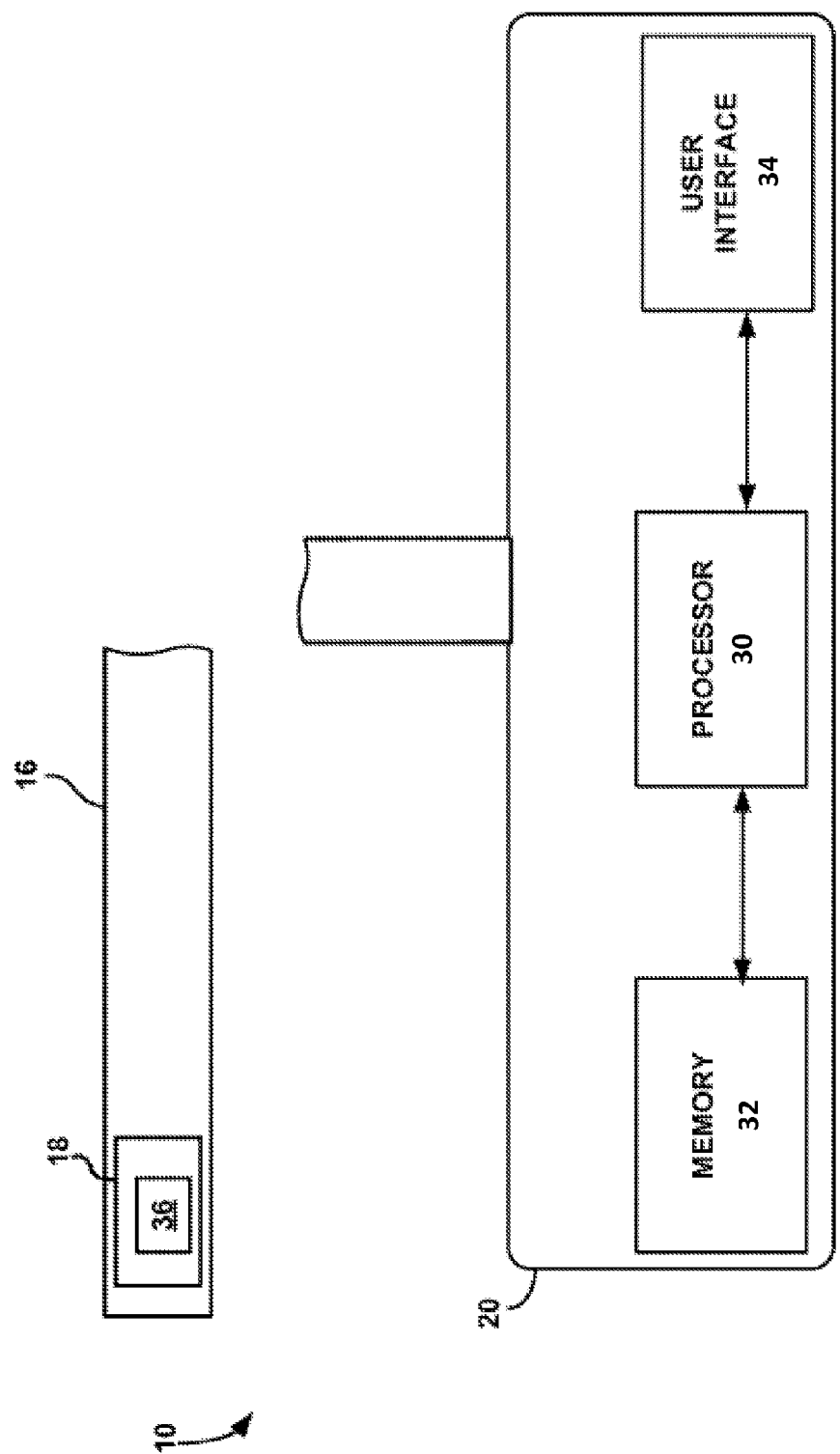
FIG. 3 is a functional block diagram illustrating an example configuration of the system of FIG. 1.

FIG. 3 is a functional block diagram illustrating example components that may be included in system 10. As shown in this example, console 20 includes a processor 30, a memory 32, and a user interface 34. Intravascular measurement device 18 includes a transducer 36 that is configured to receive reflected energy corresponding to the physical dimensions of the blood vessel into which the intravascular measurement device is inserted.

In general, memory 32 stores program instructions and related data that, when executed by processor 30, cause intravascular measurement device 18 and processor 30 to perform the functions attributed to them in this disclosure. For example, memory 32 may include non-transitory computer-readable instructions that, when executed by processor 30, cause intravascular measurement device 18 and processor 30 to perform various functions attributed to intravascular measurement device 18 and processor 30 herein. Memory 32 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 32 may store data representative of physical dimension measurements may by intravascular measurement device 18. Further, as discussed below, memory 32 may store data representative of equations and information used by processor 30 to analyze measurement information generated by intravascular measurement device 18 to determine if a stenotic lesion in patient 14 (FIG. 1) is ischemic or nonischemic.

Processor 30 may include any one or more of a microprocessor, a controller, a digital signal processor (DSP), an application specific integrated circuit (ASIC), a field-programmable gate array (FPGA), or equivalent discrete or integrated logic circuitry. In some examples, processor 30 may include multiple components, such as any combination of one or more microprocessors, one or more controllers, one or more DSPs, one or more ASICs, or one or more FPGAs, as well as other discrete or integrated logic circuitry. The functions attributed to processor 30 herein, as well as other processors referred to herein, may be embodied as software, firmware, hardware or any combination thereof.

During operation, transducer 36 may operate under the control of processor 30 to receive energy reflected from tissue surrounding intravascular measurement device 18. Transducer 36 may receive the reflected energy in response to energy that emitted from the intravascular measurement device (e.g., by an energy emitter operating under the control of processor 30). In different examples, energy received by transducer 36 may be reflected acoustical energy (e.g., ultrasonic energy), reflected optical energy, reflected magnetic energy, or the like. Transducer 36 can convert the received reflected energy into an electrical measurement signal that can be processed by processor 30 for storage on memory 32 and/or display on user interface 34. Repositioning intravascular measurement device 18 within blood vessel 22 (FIG. 2) so as to measure physical dimensions of the blood vessel at different locations (as described above with respect to FIGS. 1 and 2) can cause transducer 36 to receive reflected energy from the different locations within the vessel, thereby generating different measurement signals that can be received by processor 30.

Transducer 36 can implemented using a variety of different configurations, and the configurations of the transducer may vary based on the type of reflected energy the transducer is designed to receive. In instances in which transducer 36 is configured to receive ultrasonic acoustical energy, the transducer may comprise piezoelectric crystals that deform in response to acoustical energy at predetermined frequencies to generate electrical signals. How the crystal is manufactured can impact the frequency at which the crystal can respond. Higher frequency ultrasound energy (e.g., greater than 50 MHz) typically provides resolution that is very good, but differentiation between the blood (or other fluid) and the wall of a vessel is typically not as good. In contrast, lower frequency ultrasound energy can provide differentiation that is very good but resolution that is typically not as good.

Although transducer 36 is illustrate in FIG. 3 as being positioned within intravascular measurement device 18 and the intravascular measurement device 18 is generally described in this disclosure as being configured to measure a physical dimension of a blood vessel or other lumen of patient 14, it should be appreciated that the hardware and/or software for emitting energy, receiving reflected energy, and/or processing signals need not be physically implemented within the intravascular measurement device itself. Rather, various emitters, receivers, and/or processing hardware and software may be physically associated with catheter 16 or console 20 (FIG. 1) and communicatively coupled to intravascular measurement device 18 (e.g., via an electrical, optical, fluid, or other communication line).

Independent of the specific configuration of transducer 36, processor 30 can receive measurement signals representative of a physical dimension of blood vessel 22 (FIG. 2) at different locations and/or under different conditions (e.g., different blood flow rates) and compare determined physical dimensions to characterize stenotic lesion 24. The comparison performed by processor 30 may depend on the number of different locations in which physical dimensions of blood vessel 22 are measured and/or the different conditions under which multiple physical measurements of blood vessel 22 are taken at the same location. In some examples, processor 30 determines a value representative of a change in a physical dimension of blood vessel 22 under one condition (e.g., a first blood flow rate) and the physical dimension of the blood vessel under a different condition (e.g., a second blood flow rate higher than the first blood flow rate).

For example, processor 30 may determine a ratio of a physical dimension of blood vessel 22 under one condition (e.g., a first blood flow rate) divided by the physical dimension of the blood vessel under a different condition (e.g., a second blood flow rate higher than the first blood flow rate). In accordance with this example, processor 30 may determine the value as follows:

$$\text{Value} = A_{First\ Blood\ Flow\ Rate}^{Proximal} / A_{Second\ Blood\ Flow\ Rate}^{Proximal}, \quad \text{Equation (1):}$$

$$\text{Value} = D_{First\ Blood\ Flow\ Rate}^{Proximal} / D_{Second\ Blood\ Flow\ Rate}^{Proximal}, \quad \text{Equation (2):}$$

$$\text{Value} = A_{First\ Blood\ Flow\ Rate}^{Distal} / A_{Second\ Blood\ Flow\ Rate}^{Distal}, \quad \text{Equation (3):}$$

$$\text{Value} = D_{First\ Blood\ Flow\ Rate}^{Distal} / D_{Second\ Blood\ Flow\ Rate}^{Distal}, \quad \text{Equation (4):}$$

$$\text{Value} = MLA_{First\ Blood\ Flow\ Rate} / MLA_{Second\ Blood\ Flow\ Rate}, \text{ and} \quad \text{Equation (5):}$$

$$\text{Value} = MLD_{First\ Blood\ Flow\ Rate} / MLD_{Second\ Blood\ Flow\ Rate}. \quad \text{Equation (6):}$$

In the equations above, $A_{First\ Blood\ Flow\ Rate}^{Proximal}$ and $A_{First\ Blood\ Flow\ Rate}^{Distal}$ are cross-sectional areas of blood vessel 22 (FIG. 2) at a location proximal and a location distal, respectively, to stenotic lesion 24 at a first blood flow rate (e.g., a comparatively low blood flow rate) and $A_{Second\ Blood\ Flow\ Rate}^{Proximal}$ and $A_{Second\ Blood\ Flow\ Rate}^{Distal}$ are the cross-sectional areas of blood vessel 22 at the location proximal and the location distal, respectively, to stenotic lesion 24 at a second blood flow rate (e.g., a comparatively high blood flow rate). Further, $D_{First\ Blood\ Flow\ Rate}^{Proximal}$ and $D_{First\ Blood\ Flow\ Rate}^{Distal}$ are diameters of blood vessel 22 (FIG. 2) at a location proximal and a location distal, respectively, to stenotic lesion 24 at a first blood flow rate (e.g., a comparatively low blood flow rate) and $D_{Second\ Blood\ Flow\ Rate}^{Proximal}$ and $D_{Second\ Blood\ Flow\ Rate}^{Distal}$ are the diameter of blood vessel 22 at the location proximal and the location distal, respectively, to stenotic lesion 24 at a second blood flow rate (e.g., a comparatively high blood flow rate). In addition, $MLA_{First\ Blood\ Flow\ Rate}$ and $MLA_{Second\ Blood\ Flow\ Rate}$ are cross-sectional areas of blood vessel 22 (FIG. 2) in the region of the stenotic lesion where the blood vessel defines a minimal lumen diameter (e.g., a location where the lesion causes the maximum narrowing of the blood vessel lumen) at a first blood flow rate and a second blood flow rate, respectively. Finally, $MLD_{First\ Blood\ Flow\ Rate}$ and $MLD_{Second\ Blood\ Flow\ Rate}$ are diameters of blood vessel 22 in the region of the stenotic lesion where the blood vessel defines a minimal lumen diameter (e.g., a location where the lesion causes the maximum narrowing of the blood vessel lumen) at a first blood flow rate and a second blood flow rate, respectively.

In addition to or in lieu of determining a physical dimension of blood vessel 22 under one condition to the physical dimension of the blood vessel under a different condition, processor 30 may determine a difference between the physical dimension of blood vessel 22 under one condition (e.g., a higher blood flow rate) and the physical dimension of the blood vessel under a different condition (e.g., a lower blood flow rate). In accordance with this example, processor 30 may determine the value as follows:

$$\text{Value} = A_{First\ Blood\ Flow\ Rate}^{Proximal} - A_{Second\ Blood\ Flow\ Rate}^{Proximal}, \quad \text{Equation (7):}$$

$$\text{Value} = D_{First\ Blood\ Flow\ Rate}^{Proximal} - D_{Second\ Blood\ Flow\ Rate}^{Proximal}, \quad \text{Equation (8):}$$

$$\text{Value} = A_{First\ Blood\ Flow\ Rate}^{Distal} - A_{Second\ Blood\ Flow\ Rate}^{Distal}, \quad \text{Equation (9):}$$

$$\text{Value} = D_{First\ Blood\ Flow\ Rate}^{Distal} - D_{Second\ Blood\ Flow\ Rate}^{Distal}, \quad \text{Equation (10):}$$

$$\text{Value} = MLA_{First\ Blood\ Flow\ Rate} - MLA_{Second\ Blood\ Flow\ Rate}, \text{ and} \quad \text{Equation (11):}$$

$$\text{Value} = MLD_{First\ Blood\ Flow\ Rate} - MLD_{Second\ Blood\ Flow\ Rate}. \quad \text{Equation (12):}$$

In instances in which intravascular measurement device 18 used to make measurements of blood vessel 22 at multiple different locations under different conditions (e.g., different blood flow rates), processor 30 may compare a changes in physical dimension of the blood vessel at one location relative to a change in the physical dimension of the blood vessel at another location. For example, when intravascular measurement device 18 used to make measurements of blood vessel 22 at a location both proximal to stenotic lesion 24 and a location distal to the lesion, processor 30 may determine a value representative of a change in physical dimension at the distal location relative to the proximal location as follows:

$$\text{Value} = (D_{First\ Blood\ Flow\ Rate}^{Distal} - D_{Second\ Blood\ Flow\ Rate}^{Distal}) - (D_{First\ Blood\ Flow\ Rate}^{Proximal} - D_{Second\ Blood\ Flow\ Rate}^{Proximal}).$$  Equation (12):

$$\text{Value} = (A_{First\ Blood\ Flow\ Rate}^{Distal} - A_{Second\ Blood\ Flow\ Rate}^{Distal}) - (A_{First\ Blood\ Flow\ Rate}^{Proximal} - A_{Second\ Blood\ Flow\ Rate}^{Proximal}),$$  Equation (13):

Based on the values determined by processor 30 that are representative of the change in physical dimension of blood vessel 22 between the first condition (e.g., first blood flow rate) and the second condition (e.g., second blood flow rate), processor 30 may determine whether or not stenotic lesion 24 is ischemia inducing. For example, with reference to data stored on memory 32, processor 30 can compare the determined value to one or more reference values and determine based on the comparison whether or not stenotic lesion 24 is ischemia inducing. Processor 30 may compare the determined value to one or more reference values and, if the determined value is higher or lower than the reference value, determine whether or not stenotic lesion 24 is ischemia inducing. The reference values stored in memory may be values generated during clinical testing by measuring the physical dimensions of stenotic lesions in a statistically significant number of patients. The physical dimensions of the stenotic lesions in the patients may be measured to determine how the physical dimensions of the lesions change in response to changing conditions (e.g., blood flow rates) depending on whether or not the lesions are ischemic.

The value determined by processor 30 may be stored in memory 30, displayed on user interface 34 (in instances in which the user interface includes a display), or otherwise processed. The value may indicate whether a clinician should perform an interventional procedure (e.g., angioplasty or stent placement) on the stenotic lesion.

Various examples have been described. These and other examples are within the scope of the following claims.

The invention claimed is:

1. A method comprising:
    inserting an intravascular measurement device into a body of a patient;
    controlling the intravascular measurement device to acquire a first measurement signal, the first measurement signal being indicative of a physical dimension of a blood vessel having a stenotic lesion during a first blood flow rate, the first measurement signal comprising a first distal measurement signal indicative of the physical dimension of the blood vessel at a location distal to the stenotic lesion and a first proximal measurement signal indicative of the physical dimension of the blood vessel at a location proximal to the stenotic lesion, the location proximal to the stenotic lesion not surpassing any portion of the stenotic lesion;
    controlling the intravascular measurement device to acquire a second measurement signal, the second measurement signal being indicative of the physical dimension of the blood vessel having the stenotic lesion during a second blood flow that is greater than the first blood flow rate, the second measurement signal comprising a second distal measurement signal indicative of the physical dimension of the blood vessel at the location distal to the stenotic lesion and a second proximal measurement signal indicative of the physical dimension of the blood vessel at the location proximal to the stenotic lesion; and
    determining, with a processor, a value representative of a change in the physical dimension of the blood vessel between the first blood flow rate and the second blood flow rate based on the first measurement signal and the second measurement signal,
    wherein determining the value representative of the change in the physical dimension of the blood vessel between the first and second blood flow rates comprises (i) generating a distal dilation value by determining a difference between the physical dimension of the blood vessel at the location distal to the stenotic lesion during the second blood flow rate and the physical dimension of the blood vessel at the location distal to the stenotic lesion during the first blood flow rate, (ii) generating a proximal dilation value by determining a difference between the physical dimension of the blood vessel at the location proximal to the stenotic lesion during the second blood flow rate and the physical dimension of the blood vessel at the location proximal to the stenotic lesion during the first blood flow rate, and (iii) comparing the distal dilation value to the proximal dilation value to determine the value representative of the change in physical dimension of the blood vessel between the first and second blood flow rates.

2. The method of claim 1, wherein the first blood flow rate is a blood flow rate during a first part of a patient cardiac cycle, the second blood flow rate is a blood flow rate during a second part of the patient cardiac cycle that is different than the first part of the patient cardiac cycle, the second part of the patient cardiac cycle being a part in which vascular resistance is minimized during the patient cardiac cycle.

3. The method of claim 1, wherein
    the intravascular measurement device is an intravascular ultrasonic measurement device;
    the first blood flow rate is a non-hyperemic blood flow rate; and
    the second blood flow rate is a hyperemic blood flow rate caused by a pharmacologic vasodilator drug.

4. The method of claim 1, wherein the first blood flow rate is a non-hyperemic blood flow rate and the second blood flow rate is a hyperemic blood flow rate caused by a pharmacologic vasodilator drug.

5. The method of claim 1, wherein the intravascular measurement device is an intravascular optical measurement device.

6. The method of claim 1, wherein the intravascular measurement device is an intravascular ultrasonic measurement device.

7. The method of claim 1, further comprising determining, with the processor, whether the lesion is an ischemia-inducing lesion based on the comparison between the distal dilation value and the proximal dilation value.

8. The method of claim 7, wherein the physical dimension of the blood vessel is at least one of a cross-sectional area of the blood vessel or a diameter of the blood vessel.

9. The method of claim 8, wherein, based on the comparison between the distal dilation value and the proximal dilation value, the lesion is determined to be an ischemia-inducing lesion when the distal dilation value is different than the proximal dilation value.

10. The method of claim 9, wherein the lesion is determined to be an ischemia-inducing lesion when the distal dilation value is smaller than the proximal dilation value.

11. The method of claim 1, wherein the blood vessel is a coronary artery.

12. The method of claim 1, wherein comparing the distal dilation value to the proximal dilation value to determine the value representative of the change in physical dimension of the blood vessel between the first and second blood flow rates comprises determining a ratio of the distal dilation value to the proximal dilation value.

13. The method of claim 1, wherein comparing the distal dilation value to the proximal dilation value to determine the value representative of the change in physical dimension of the blood vessel between the first and second blood flow rates comprises determining a difference between the distal dilation value and proximal dilation value.

14. A system comprising:
an intravascular measurement device configured to acquire first and second measurement signals;
a catheter configured to deliver the intravascular measurement device to a desired location in a body of a patient; and
a processor that is configured to:
receive the first measurement signal from the intravascular measurement device, the first measurement signal being indicative of a physical dimension of a blood vessel having a stenotic lesion during a first blood flow rate, the first measurement signal comprising a first distal measurement signal indicative of the physical dimension of the blood vessel at a location distal to the stenotic lesion and a first proximal measurement signal indicative of the physical dimension of the blood vessel at a location proximal to the stenotic lesion, the location proximal to the stenotic lesion not surpassing any portion of the stenotic lesion;
receive the second measurement signal from the intravascular measurement device, the second measurement signal being indicative of the physical dimension of the blood vessel having the stenotic lesion during a second blood flow rate that is greater than the first blood flow rate, the second measurement signal comprising a second distal measurement signal indicative of the physical dimension of the blood vessel at the location distal to the stenotic lesion and a second proximal measurement signal indicative of the physical dimension of the blood vessel at the location proximal to the stenotic lesion; and
determine a value representative of a change in the physical dimension of the blood vessel between the first blood flow rate and the second blood flow rate based on the first measurement signal and the second measurement signal by (i) generating a distal dilation value by determining a difference between the physical dimension of the blood vessel at the location distal to the stenotic lesion during the second blood flow rate and the physical dimension of the blood vessel at the location distal to the stenotic lesion during the first blood flow rate, (ii) generating a proximal dilation value by determining a difference between the physical dimension of the blood vessel at the location proximal to the stenotic lesion during the second blood flow rate and the physical dimension of the blood vessel at the location proximal to the stenotic lesion during the first blood flow rate, and (iii) comparing the distal dilation value to the proximal dilation value to determine the value representative of the change in physical dimension of the blood vessel between the first and second blood flow rates.

15. The system of claim 14, wherein the physical dimension is at least one of a cross-sectional area of the blood vessel or a diameter of the blood vessel.

16. The system of claim 14, wherein the intravascular measurement device is an intravascular ultrasonic measurement device, the first blood flow rate is a non-hyperemic blood flow rate, and the second blood flow rate is a hyperemic blood flow rate.

17. A non-transitory computer-readable medium comprising instructions for causing a programmable processor to:
receive a first measurement signal from an intravascular measurement device inserted into a body of a patient and configured to acquire the first measurement signal, the first measurement signal being indicative of a physical dimension of a blood vessel having a stenotic lesion during a first blood flow rate, the first measurement signal comprising a first distal measurement signal indicative of the physical dimension of the blood vessel at a location distal to the stenotic lesion and a first proximal measurement signal indicative of the physical dimension of the blood vessel at a location proximal to the stenotic lesion, the location proximal to the stenotic lesion not surpassing any portion of the stenotic lesion;
receive a second measurement signal from the intravascular measurement device inserted into the body of the patient and configured to acquire the second measurement signal, the second measurement signal being indicative of the physical dimension of the blood vessel having the stenotic lesion during a second blood flow that is greater than the first blood flow rate, the second measurement signal comprising a second distal measurement signal indicative of the physical dimension of the blood vessel at the location distal to the stenotic lesion and a second proximal measurement signal indicative of the physical dimension of the blood vessel at the location proximal to the stenotic lesion; and
determine a value representative of a change in the physical dimension of the blood vessel between the first blood flow rate and the second blood flow rate based on the first measurement signal and the second measurement signal by (i) generating a distal dilation value by determining a difference between the physical dimension of the blood vessel at the location distal to the stenotic lesion during the second blood flow rate and the physical dimension of the blood vessel at the location distal to the stenotic lesion during the first blood flow rate, (ii) generating a proximal dilation value by determining a difference between the physical dimension of the blood vessel at the location proximal to the stenotic lesion during the second blood flow rate and the physical dimension of the blood vessel at the location proximal to the stenotic lesion during the first blood flow rate, and (iii) comparing the distal dilation value to the proximal dilation value to determine the value representative of the change in physical dimension of the blood vessel between the first and second blood flow rates.

18. The computer-readable medium of claim 17, wherein the physical dimension is at least one of a cross-sectional area of the blood vessel or a diameter of the blood vessel.

19. A method comprising:
inserting an intravascular measurement device into a body of a patient;

measuring via the intravascular measurement device a first physical dimension of a blood vessel having a stenotic lesion during a first part of a patient cardiac cycle, the first physical dimension measured at a location distal to the stenotic lesion;

measuring via the intravascular measurement device a second physical dimension of the blood vessel having the stenotic lesion during a second part of the patient cardiac cycle that is different than the first part of the patient cardiac cycle, the second physical dimension measured at the location distal to the stenotic lesion;

generating a distal dilation value by comparing the second physical dimension and the first physical dimension;

measuring via the intravascular measurement device a third physical dimension of the blood vessel having the stenotic lesion during the first part of the patient cardiac cycle at a location proximal to the stenotic lesion, the location proximal to the stenotic lesion not surpassing any portion of the stenotic lesion;

measuring via the intravascular measurement device a fourth physical dimension of the blood vessel having the stenotic lesion during the second part of the patient cardiac cycle at the location proximal to the stenotic lesion;

generating a proximal dilation value by comparing the fourth physical dimension and the third physical dimension; and determining, with a processor, a value representative of a change in physical dimension of the blood vessel between the first part of the patient cardiac cycle and the second part of the patient cardiac cycle using the distal dilation value and the proximal dilation value.

20. The method of claim 19, wherein generating the distal dilation value by comparing the second physical dimension and the first physical dimension comprises determining a difference between the second physical dimension and the first physical dimension; and generating the proximal dilation value by comparing the fourth physical dimension and the third physical dimension comprises determining a difference between the fourth physical dimension and the third physical dimension.

21. The method of claim 20, wherein using the distal dilation value and the proximal dilation value to determine the value representative of the change in physical dimension of the blood vessel between the first part of the patient cardiac cycle and the second part of the patient cardiac cycle comprises determining a difference between the distal dilation value and the proximal dilation value.

22. The method of claim 21, further comprising determining, with the processor, whether the lesion is an ischemia-inducing lesion based on the difference between the distal dilation value and the proximal dilation value.

23. The method of claim 19, wherein the second part of the patient cardiac cycle is a part in which vascular resistance is minimized during the patient cardiac cycle, and wherein the first part of the patient cardiac cycle corresponds to a first blood flow rate and the second part of the patient cardiac cycle corresponds to a second blood flow rate that is different than the first blood flow rate.

* * * * *